(12) United States Patent
Husmark et al.

(10) Patent No.: US 9,510,808 B2
(45) Date of Patent: Dec. 6, 2016

(54) FLUID SAMPLING DEVICE AND METHOD FOR SAMPLING

(75) Inventors: Ulrika Husmark, Mölnlycke (SE); Ingrid Gustafson, Åsa (SE)

(73) Assignee: SCA HYGIENE PRODUCTS AB, Göteborg (SE)

(*) Notice: Subject to any disclaimer, the term of this patent is extended or adjusted under 35 U.S.C. 154(b) by 0 days.

(21) Appl. No.: 14/389,045

(22) PCT Filed: Mar. 30, 2012

(86) PCT No.: PCT/SE2012/050359
§ 371 (c)(1),
(2), (4) Date: Sep. 29, 2014

(87) PCT Pub. No.: WO2013/147662
PCT Pub. Date: Oct. 3, 2013

(65) Prior Publication Data
US 2015/0051510 A1   Feb. 19, 2015

(51) Int. Cl.
| | | |
|---|---|---|
| *A61F 13/551* | (2006.01) | |
| *A61F 13/84* | (2006.01) | |
| *A61F 13/505* | (2006.01) | |
| *A61F 13/539* | (2006.01) | |
| *A61F 13/49* | (2006.01) | |
| *A61B 10/00* | (2006.01) | |

(Continued)

(52) U.S. Cl.
CPC .............. *A61B 10/007* (2013.01); *A61F 13/49* (2013.01); *A61F 13/505* (2013.01); *A61F 13/539* (2013.01); *A61F 13/5512* (2013.01); *A61F 13/84* (2013.01); *G01N 33/493* (2013.01); *A61F 2013/15146* (2013.01); *A61F 2013/8473* (2013.01); *F04C 2270/041* (2013.01)

(58) Field of Classification Search
None
See application file for complete search history.

(56) References Cited

U.S. PATENT DOCUMENTS

| 3,814,670 A | 6/1974 | Freake et al. |
|---|---|---|
| 3,918,433 A | 11/1975 | Fuisz |

(Continued)

FOREIGN PATENT DOCUMENTS

| CN | 1806763 | 7/2006 |
|---|---|---|
| CN | 101918531 | 12/2010 |

(Continued)

OTHER PUBLICATIONS

International Search Report (PCT/ISA/210) mailed on Dec. 20, 2012, by the Swedish Patent Office as the International Searching Authority for International Application No. PCT/SE2012/050359.

(Continued)

*Primary Examiner* — Karen Cochrane Carlson
*Assistant Examiner* — Jennifer M. H. Tichy
(74) *Attorney, Agent, or Firm* — Buchanan Ingersoll & Rooney PC

(57) ABSTRACT

A urine sampling device including: a transparent sheet including two layers, namely, a urine sampling layer and a support layer, wherein the urine sampling layer has liquid receiving and retaining properties by means of capillary forces and/or diffusion, and the device is arranged such that it can be positioned on the body side of an hygiene absorbent product. Also, a urine sampling arrangement and a urine sampling system, including the device. And, a hygiene absorbent product including the device, and a method for using the device.

19 Claims, 14 Drawing Sheets

Figure 1:
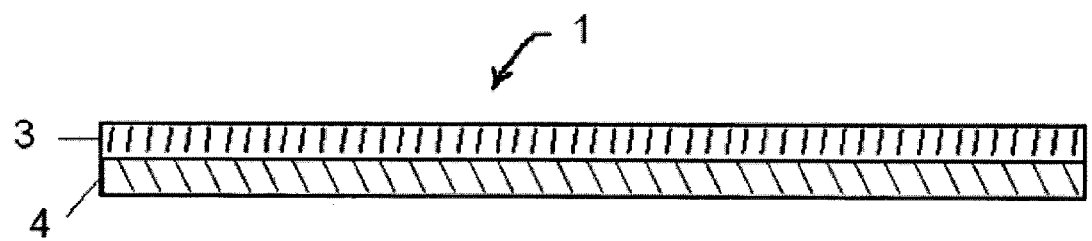

(51) Int. Cl.
*G01N 33/493* (2006.01)
*A61F 13/15* (2006.01)

(56) References Cited

U.S. PATENT DOCUMENTS

| | | | |
|---|---|---|---|
| 4,587,213 | A | 5/1986 | Malecki |
| 4,700,714 | A | 10/1987 | Fuisz |
| 5,494,823 | A | 2/1996 | Takemoto et al. |
| 6,387,708 | B2 | 5/2002 | Wardlaw |
| 6,632,661 | B2 | 10/2003 | Wickert |
| 2008/0269706 | A1 | 10/2008 | Long et al. |
| 2008/0269707 | A1 | 10/2008 | Song |
| 2008/0274014 | A1 | 11/2008 | Jumonville et al. |
| 2009/0007326 | A1 | 1/2009 | Bozic |
| 2009/0143754 | A1 | 6/2009 | Boga et al. |
| 2009/0275906 | A1 | 11/2009 | Berland et al. |
| 2011/0145993 | A1 | 6/2011 | Rader et al. |
| 2012/0028297 | A1 | 2/2012 | Zook et al. |
| 2012/0288888 | A1 | 11/2012 | Miller et al. |

FOREIGN PATENT DOCUMENTS

| | | |
|---|---|---|
| EP | 1 079 224 A2 | 2/2001 |
| JP | 2002306522 | 10/2002 |
| WO | 00-49948 A2 | 8/2000 |
| WO | WO 02/46353 A2 | 6/2002 |
| WO | 03009798 | 2/2003 |
| WO | 2007-076558 A1 | 7/2007 |
| WO | WO 2008/131904 A2 | 11/2008 |
| WO | WO 2009/108229 A2 | 9/2009 |
| WO | WO 2011/082305 A1 | 7/2011 |
| WO | 2012019214 | 2/2012 |

OTHER PUBLICATIONS

Written Opinion (PCT/ISA/237) mailed on Dec. 20, 2012, by the Swedish Patent Office as the International Searching Authority for International Application No. PCT/SE2012/050359.
International Preliminary Report on Patentability (PCT/IPEA/409) mailed on Feb. 5, 2014, by the Swedish Patent Office as the International Searching Authority for International Application No. PCT/SE2012/050359.
Notification of First Office Action issued in corresponding Chinese Patent Application No. 201280072162.5, dated Aug. 21, 2015; only English translation attached (12 pages).
Supplementary European Search Report issued in corresponding European Patent Application No. 12872731.0, dated Oct. 16, 2015 (7 pages).
Australian Office Action (Patent Examination Report No. 1) issued on Feb. 25, 2015, by the Australian Patent Office in corresponding Australian Patent Application No. 2012375452. (4 pages).

FLUID SAMPLING DEVICE AND METHOD FOR SAMPLING

CROSS REFERENCE TO RELATED APPLICATIONS

The present application is a U.S. National Stage Application of International Application No. PCT/SE2012/050359, filed on Mar. 30, 2012. The entire contents of International Application No. PCT/SE2012/050359 are hereby incorporated herein by reference in their entirety.

TECHNICAL FIELD

An embodiment of the disclosure relates to a urine sampling device. An embodiment of the disclosure relates to a urine sampling arrangement and a urine sampling system. An embodiment of the disclosure relates to a hygiene absorbent product provided with such a device, and further to a method of using the urine sampling device or arrangement and hygiene absorbent product.

KNOWN ART

A lateral flow device is known from US 2008 269707 A1. This device gives the possibility to sample urine in an absorbent article and uses a chromatographic medium that defines a detection zone. The detection zone provides a signal indicative of the presence or absence of an analyte. The device cannot be used for further more precise testing.

From SE 532 682 C2, a diaper is known with a container for sampling of urine. The container is positioned on the outside of diaper. The diaper can be used for analysis of amounts of urine that is produced over a predetermined time period as well as for collection of urine in liquid state for further analysis.

SUMMARY

The known art does not solve the problem of providing a simplification of the urine sampling device that provides a simple and effective way of making a precise analysis of a urine sample.

This problem addressed by an embodiment of the disclosure in that there is provided a urine sampling device comprising:
  a transparent sheet comprising two layers;
  a urine sampling layer; and
  a support layer,
  wherein the urine sampling layer has liquid receiving and retaining properties by means of capillary forces and/or diffusion, and the device is arranged such that it can be positioned on the body side of a hygiene absorbent product.

The advantage of the device is that the urine that is sampled will be of a volume that only varies within a small interval, such that the concentration of the analyte which is desired to test is not affected considerably. Specifically this analyte is bacteria and the precise amount of sample volume ensures that the number of CFU/ml is not affected considerably. Thereby, the device provides for a precise analysis of the type and amount of bacteria that is present. And further as the device is transparent, when the device is applied to a cultivation device it can be turned such that the urine sampling layer is applied directly to the cultivation device. After growth, the bacteria colonies can then be counted swiftly and directly through the urine sampling device. A further advantage is that the device can be applied to a hygiene absorbent product, such that urine sampling from patients that cannot provide samples on demand, for example infants and demented adults, is simplified.

According to a further development the device, by being transparent, allows direct cultivation. As mentioned above one of the main advantages is that the device which is sampling can be used directly for a quantitative analysing of bacteria that is sampled. In accordance with a further development the urine sampling layer has no auxiliary addition of bacteria nutrients. This is to avoid unnecessary bacterial growth during use of the absorbent product.

In accordance with a further development of an embodiment of the disclosure, the urine sampling layer comprises a hydrogel in the form of a film, preferably dry film, or a foam. The advantage of using a hydrogel is that the sampling of the urine is performed until the gel is saturated, thus the amount of urine is essentially controlled to a predetermined amount. The sampled bacteria are retained in place. Another advantage is that wetted hydrogels are generally transparent and thus this provides the device with the desired property of transparency for the further analysis of the sampled urine.

In accordance with a further development of an embodiment of the disclosure, the urine sampling layer comprises a liquid retaining material, chosen from a group consisting of polysaccharides or synthetic polymers, wherein the polymers are preferably hydrophilic polymers. The advantage of polysaccharides is that they come from a renewable source, which is considered beneficial for the environment, not least by the consumers. The advantage of synthetic polymers is that they are homogeneous in composition from batch to batch.

In accordance with a further development of an embodiment of the disclosure, the urine sampling device comprises a flap for removal of the device from a hygiene absorbent product and for positioning the device on a cultivating device, after a urine sample has been collected. The advantage of the flap is that the removal is facilitated. Another advantage is that the contamination risk is minimized as the person removing the urine sampling device from a hygiene absorbent product need not be in direct contact with the device. Another advantage is that when positioning the device on a cultivation device the person making the positioning need not be in direct contact with neither the urine sampling device nor the cultivation device. Another advantage is that the flap eliminates the usage of a tool such as a tweezers that need to be sterilized and that could damage the urine sampling layer.

In accordance with a further development of an embodiment of the disclosure, the support layer is provided with a transparent attachment means. The advantage of this is that the device can be removed from a hygiene absorbent product and used for analysis, without any further removal of the attachment means from the urine sampling device. In a further embodiment the attachment means is provided in the form of a transparent adhesive. This has the advantage that it facilitates the process of manufacturing the device as the adhesive can be easily applied. In a further development the attachment means is arranged such that it can be detached from for example a hygiene absorbent product. This provides for an easy operation with the device as it can be detached without using a tool, such as a pair of scissors.

In another embodiment, the fluid sampling device is provided with a carrier layer positioned on the urine sampling layer, this layer being preferably formed by a nonwoven fabric. The carrier layer may improve the wicking of the fluid that is received by the device when using it for fluid sampling. And further it provides an improved comfort for a user. The carrier layer also has an advantage that it reduces splashing when the fluid hits the device.

In another embodiment, the carrier layer is provided with attachment means for detachably attaching it to the urine sampling layer. This has the advantage that when the urine sampling device is to be used for cultivation the carrier layer can be easily removed.

In a further development, the device as discussed above has a size that is adapted to a cultivation device, such that the device can be applied directly to the cultivation device. This provides for easy handling and convenient analysis of bacteria in the urine that has been collected.

In a further development, the support layer of the device comprises a grid pattern. This has the advantage that when applied to a cultivation device no extra grid needs to be provided in order to count the bacteria colonies that are grown.

In a further development, a urine sampling arrangement is provided, in said arrangement preferably two or more fluid sampling devices have been attached to a carrier layer such that the group of devices can be employed together. The advantage of this is that the process of sampling can be improved. A double or a triple sample from the same person can be sampled easily at the same moment, yet cultivated separately for an accurate determination of the patient's condition. By using a urine sampling arrangement according to an embodiment of the disclosure, the removal handling of the urine sampling devices is thus improved. It is further possible to use one device for determining the total number of aerobe bacteria, and selective devices for enumeration of specific species or groups of bacteria.

In another embodiment of the disclosure a urine sampling system is provided comprising a urine sampling device or arrangement as discussed above, and further comprising a container for housing the device and or arrangement when transporting it to a cultivation site, further comprising a cultivation device. The system provides for a complete kit that can be used for the analysis of a patient's condition without adding any further equipment, thus providing a convenient and easy to operate analysis system.

In a further development of the system above, the urine sampling device has essentially the same size and form as the cultivation device, thereby contamination risks when applying said urine sampling device to said cultivation device can be minimized. In a further development the cultivation device comprises a grid pattern.

An embodiment of the disclosure further provides for a hygiene absorbent product comprising a urine sampling device or a urine sampling arrangement as discussed above. This provides for a simple operation of the device or arrangement of an embodiment of the disclosure where it is already applied to a hygiene absorbent product for direct application on the person to be examined.

An embodiment of the disclosure further provides a method for sampling urines for analysis comprising the steps of:
  a applying a device according to the above, to a hygiene absorbent product;
  b applying the hygiene absorbent product as modified to a user;
  c await delivery of urine from the user;
  d removing the hygiene absorbent product from the user; and
  e removing the device from the hygiene absorbent product;
  or
  a1 applying an urine sampling arrangement according to the above, to a hygiene absorbent product;
  b1 applying the hygiene absorbent product as modified to a user;
  c1 await delivery of urine from the user;
  d1 removing the hygiene absorbent product from the user; and
  e1 removing the arrangement from the hygiene absorbent product;
  or
  a2 providing a hygiene absorbent product comprising a device or arrangement according to the above;
  b2 applying the hygiene absorbent product to a user;
  c2 await delivery of urine from the user;
  d2 removing the hygiene absorbent product from the user; and
  e2 removing the device or arrangement from the hygiene absorbent product.

In a further development of the method the following steps are provided in the method:
  f applying the device to a cultivation device with the urine sampling layer positioned on the cultivation device;
  g cultivating the sample under predetermined controlled conditions; and
  h determining the amount of bacteria in the sample by controlling the number of colonies counted through the transparent device;
  or
  f1 applying the arrangement to a cultivation device with the urine sampling layer positioned on the cultivation device;
  g1 cultivating the sample under predetermined controlled conditions; and
  h1 determining the amount of bacteria in the sample by controlling the number of colonies counted through the transparent device.

LIST OF DRAWINGS

FIG. 1 discloses a first embodiment of the urine sampling device in a cross section.

Figure 2:
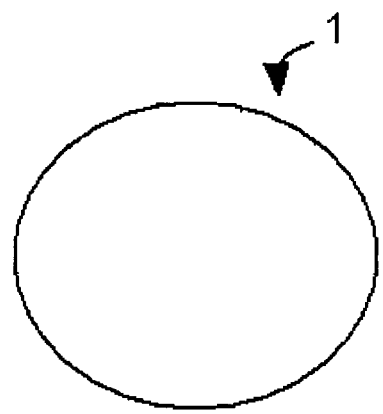

FIG. 2 discloses the first embodiment.

Figure 3:
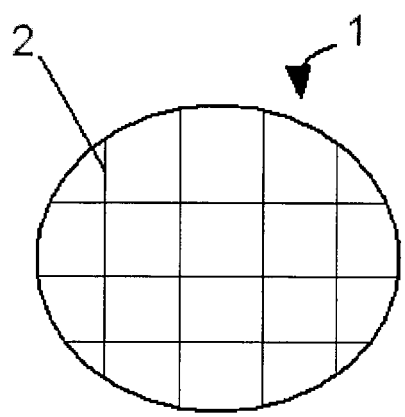

FIG. 3 discloses the first embodiment provided with a grid pattern.

Figure 4:
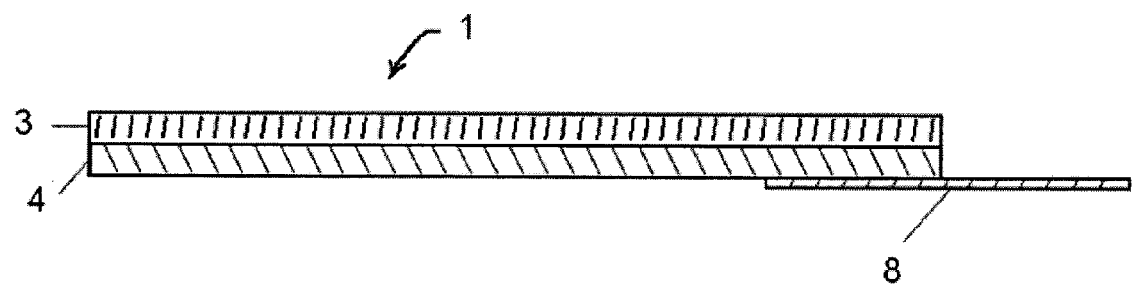

FIG. 4 discloses the first embodiment provided with a flap in a cross section.

Figure 5:
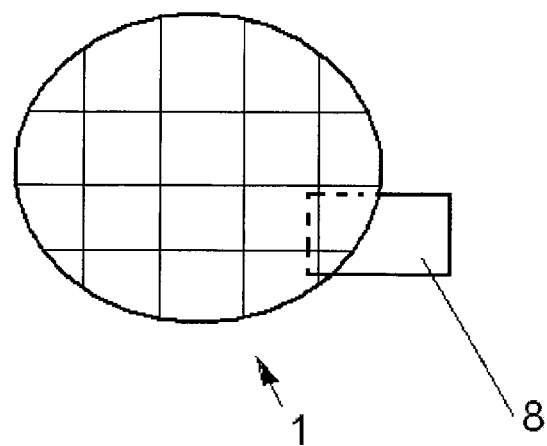

FIG. 5 discloses the first embodiment provided with a flap.

Figure 6:
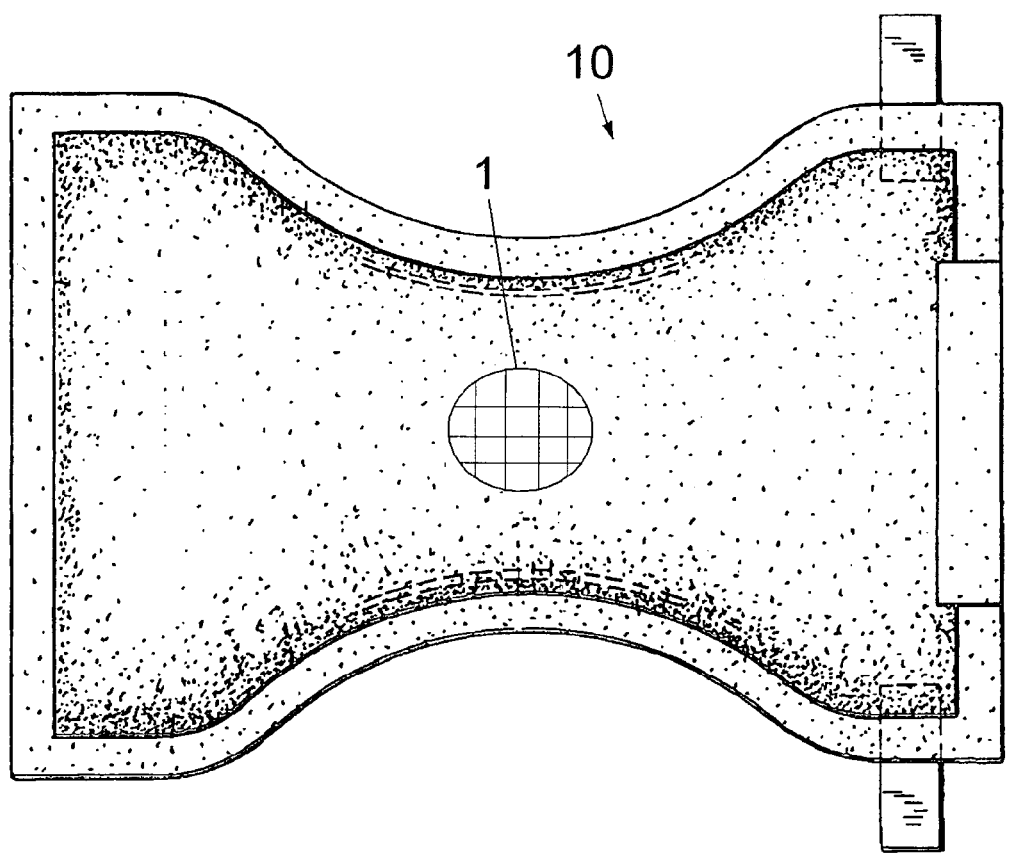

FIG. 6 discloses a urine sampling device applied to a hygiene absorbent product.

Figure 7:
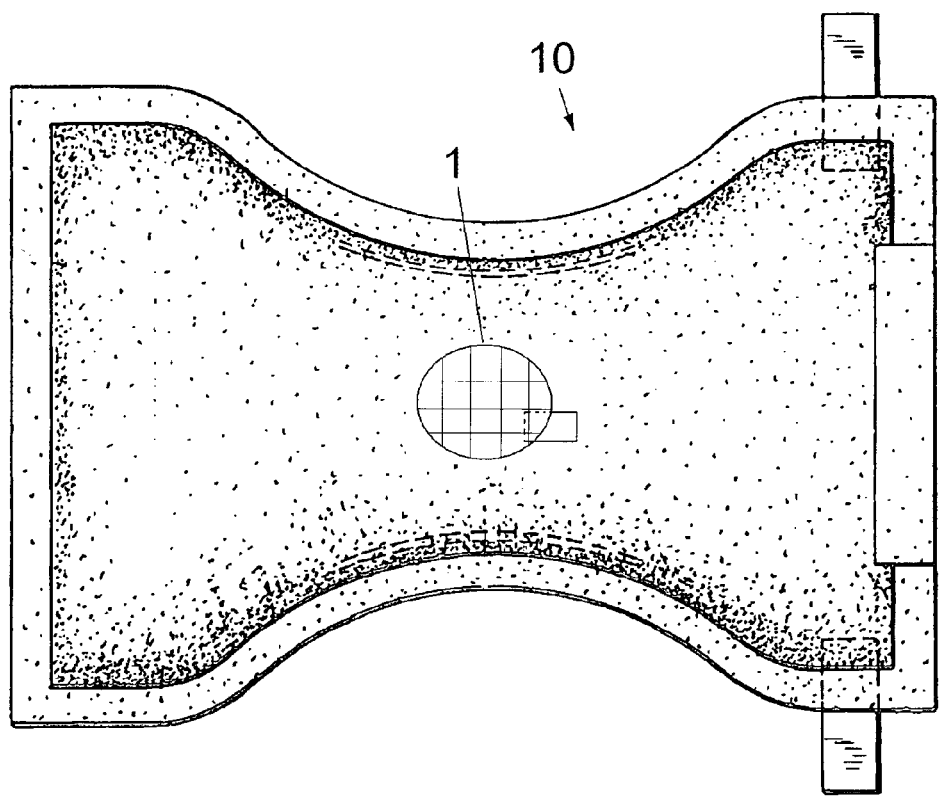

FIG. 7 discloses the embodiment of FIG. 5 applied to a hygiene absorbent product.

Figure 8:
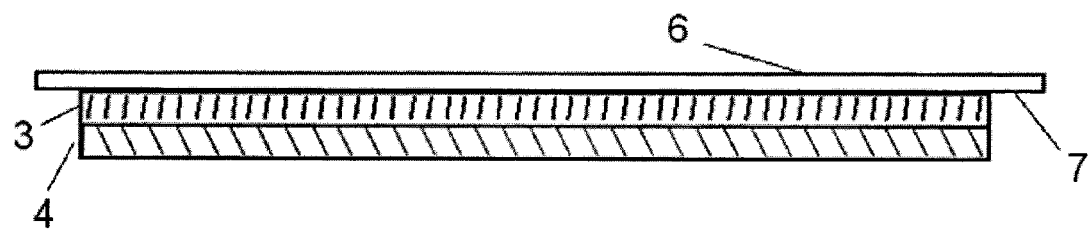

FIG. 8 discloses another embodiment of the fluid sampling device comprising a carrier layer.

Figure 9:
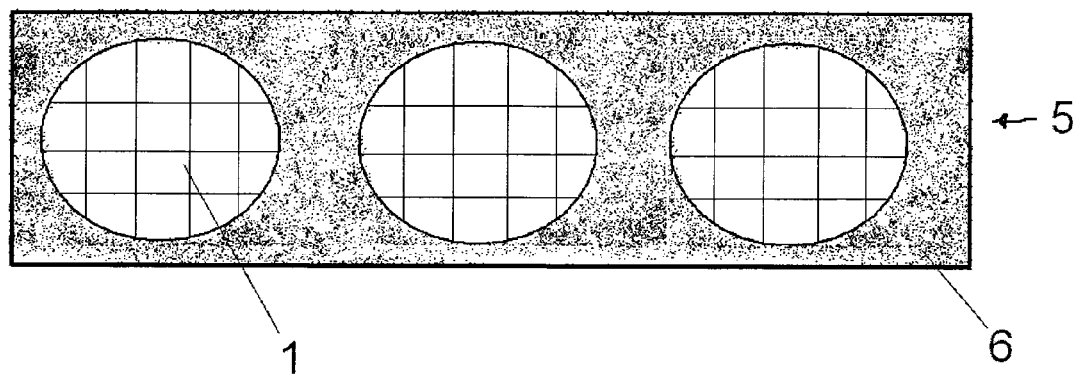

FIG. 9 discloses a urine sampling arrangement.

Figure 10:
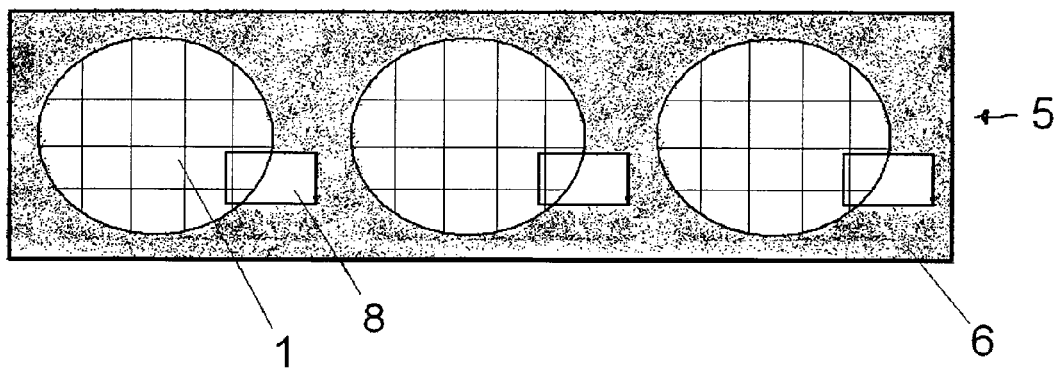

FIG. 10 discloses a urine sampling arrangement comprising flaps.

Figure 11:
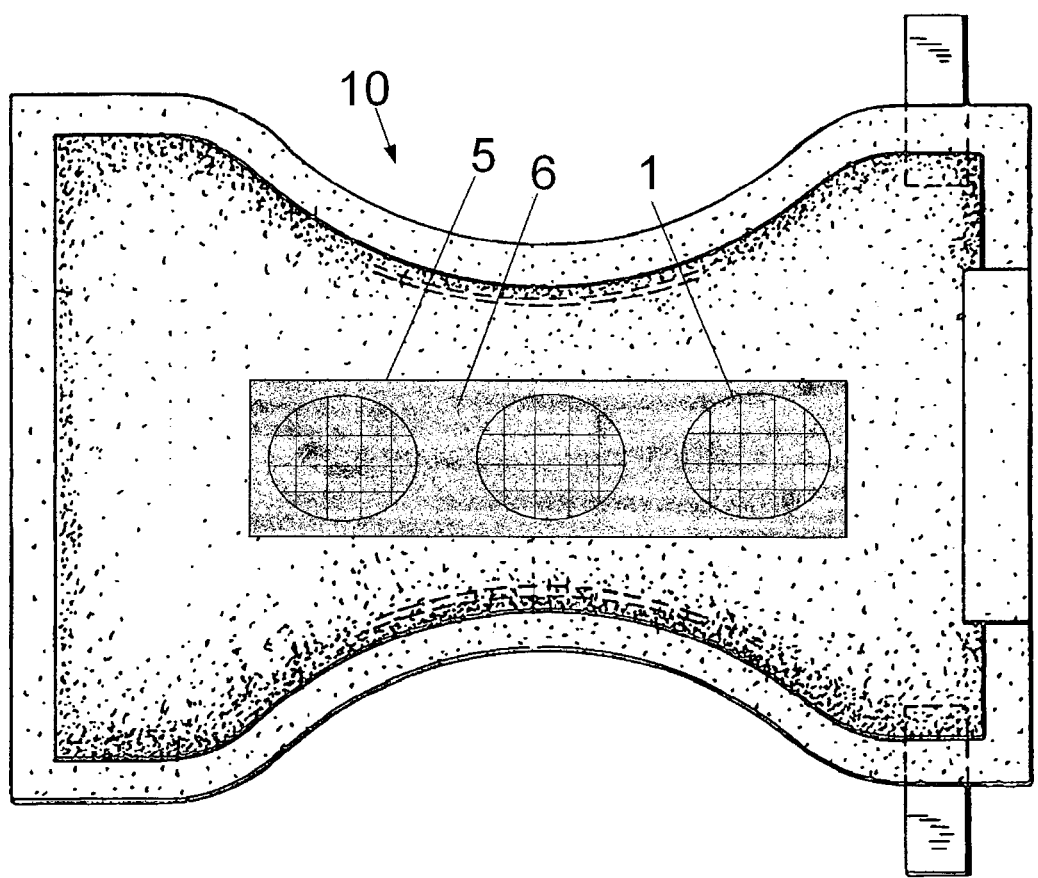

FIG. 11 discloses a urine sampling arrangement attached to a hygiene absorbent product.

Figure 12:
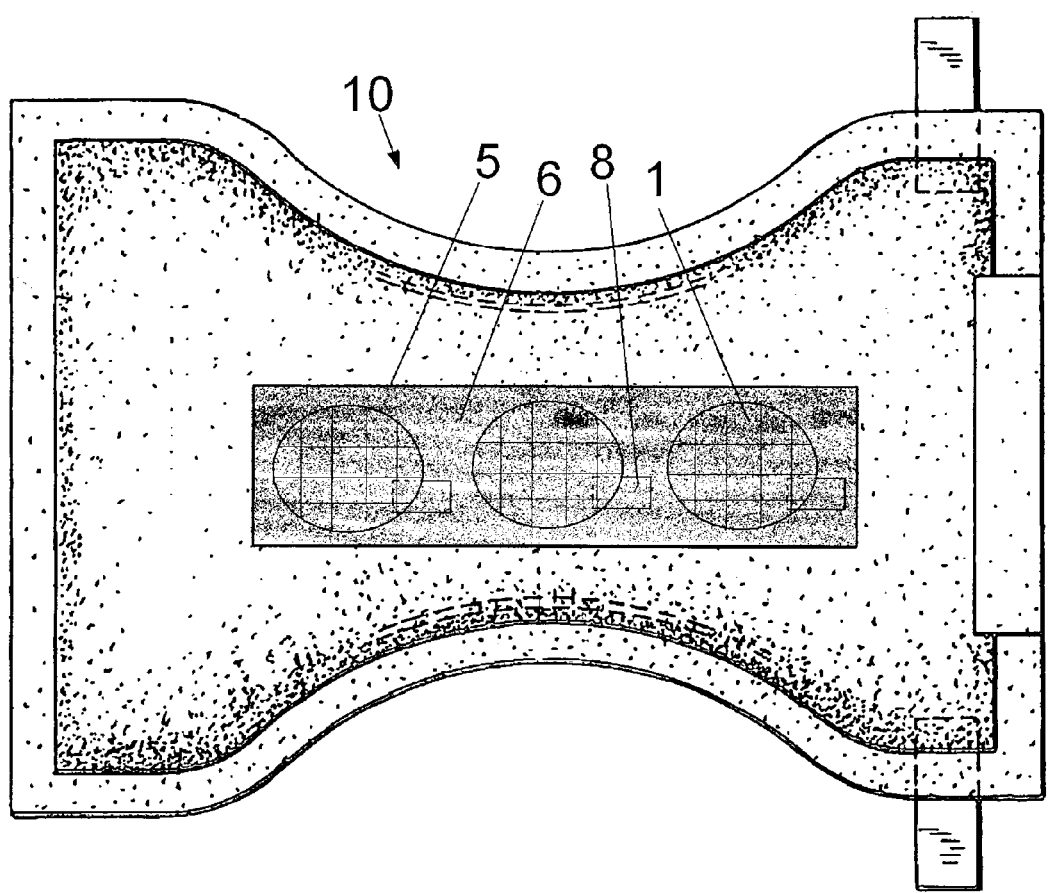

FIG. 12 discloses a urine sampling arrangement of FIG. 10 attached to a hygiene absorbent product.

Figure 13:
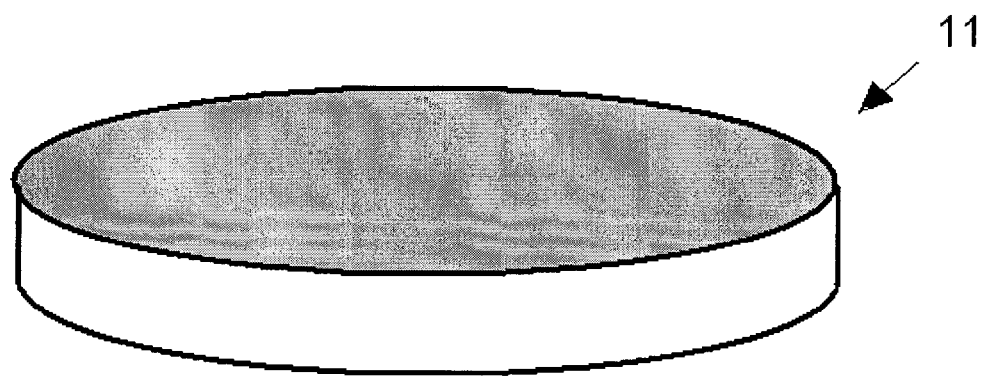

FIG. 13 discloses a cultivation device to be used with an embodiment of the disclosure.

Figure 14:
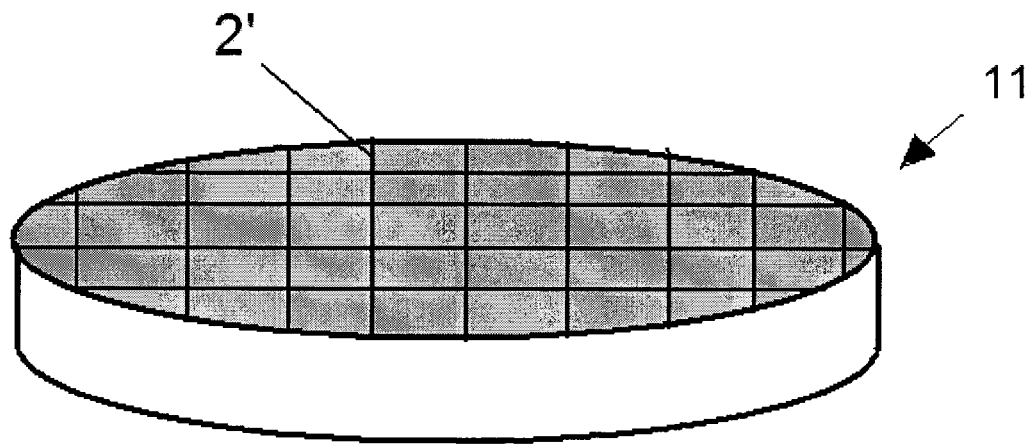

FIG. 14 discloses a cultivation device to be used with an embodiment of the disclosure comprising a grid pattern.

Figure 15:
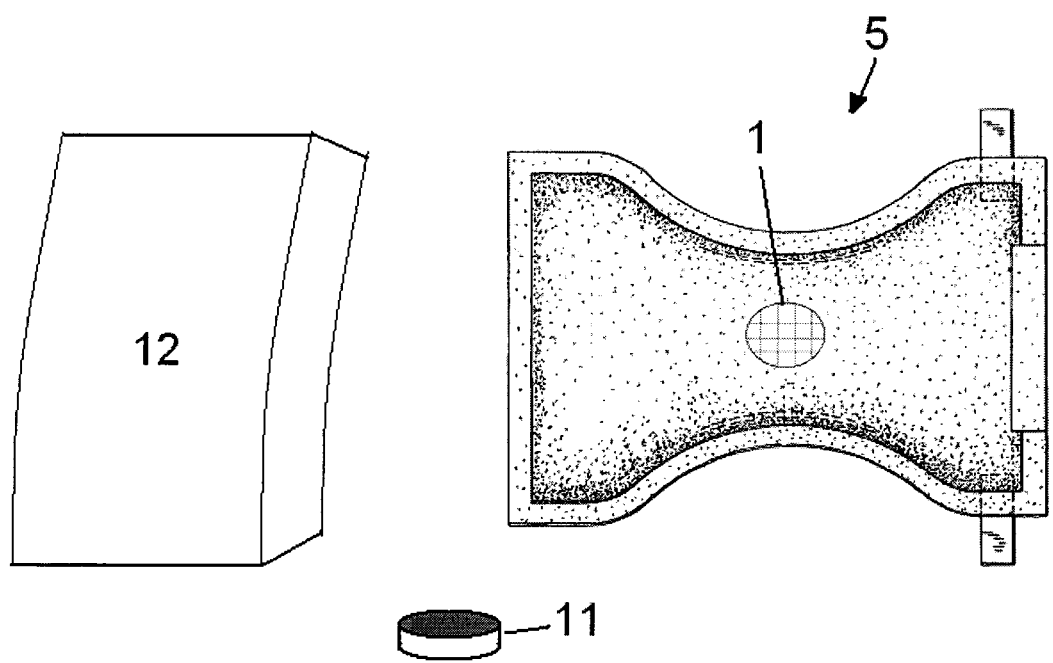

FIG. 15 discloses a urine sampling system according to an embodiment of the disclosure.

Figure 16:
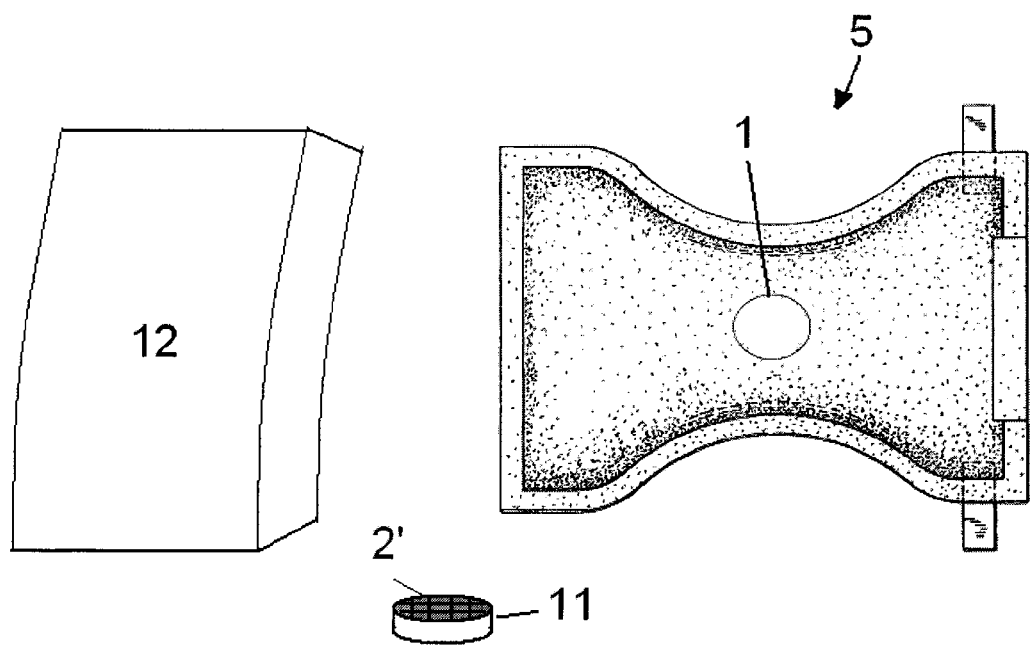

FIG. 16 discloses a urine sampling system according to an embodiment of the disclosure, with grid pattern on the cultivation device.

Figure 17:
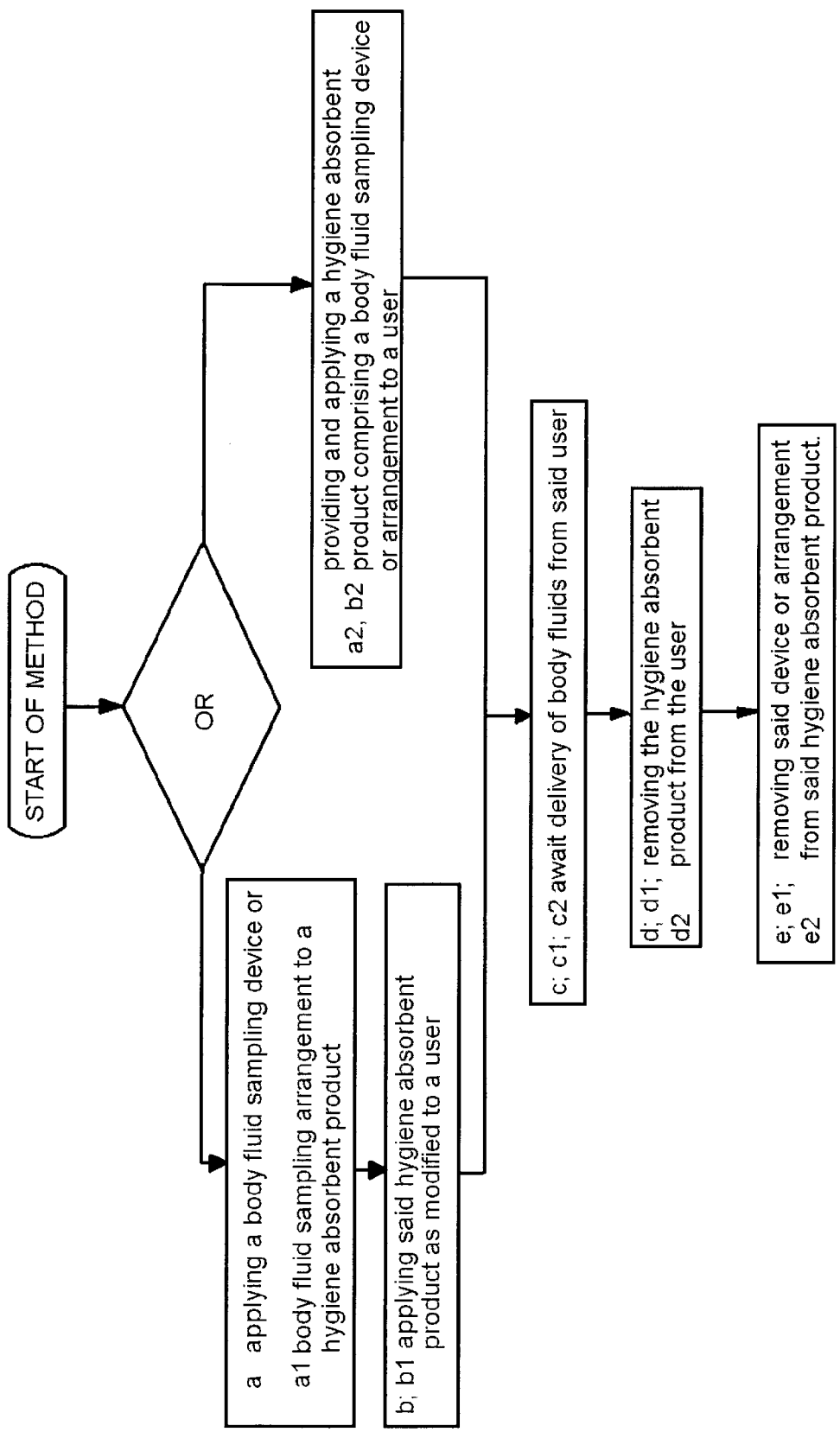

FIG. 17 discloses a flow diagram of the method according to an embodiment of the disclosure.

Figure 18:
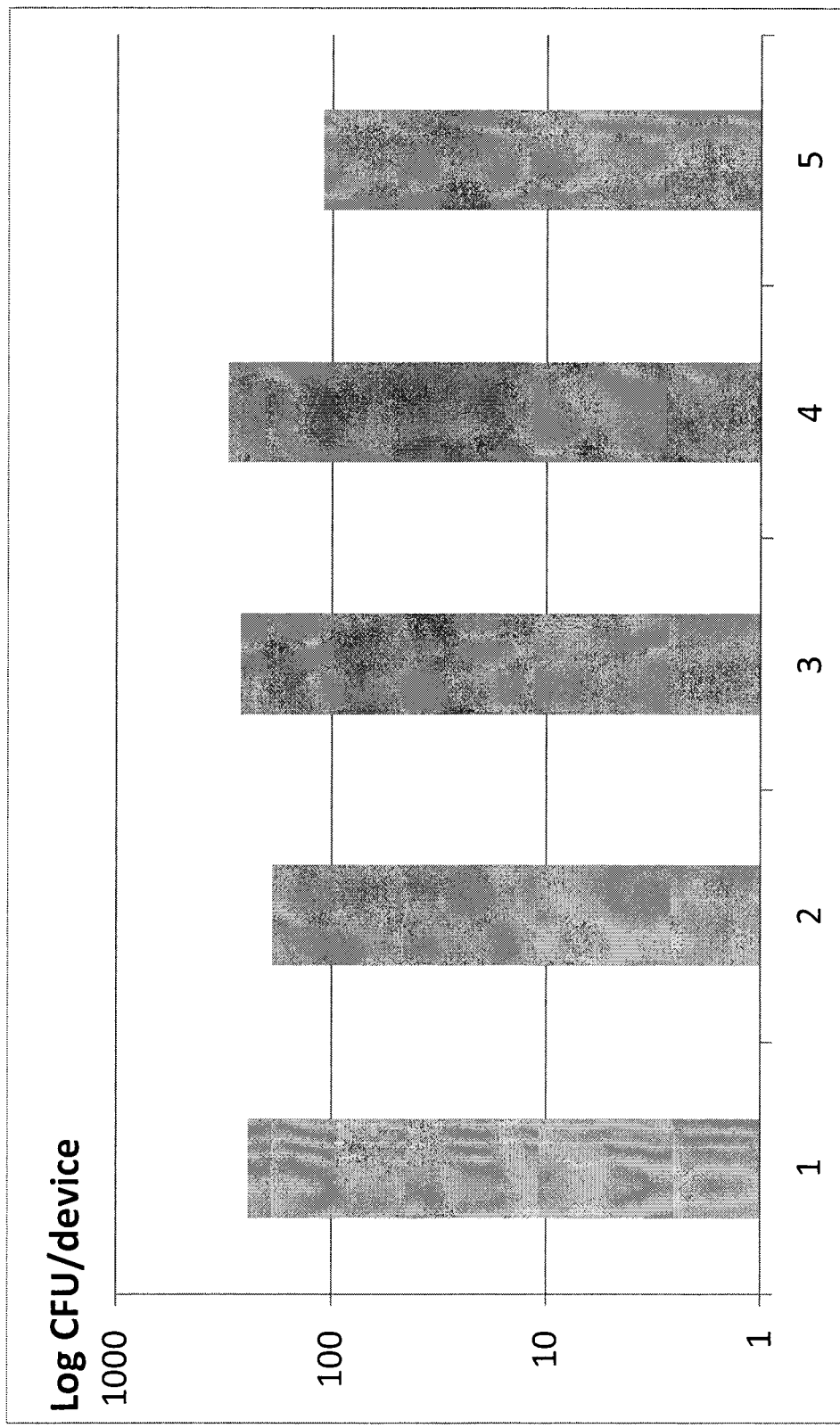

FIG. 18 discloses a chart for Example 1.

Figure 19:
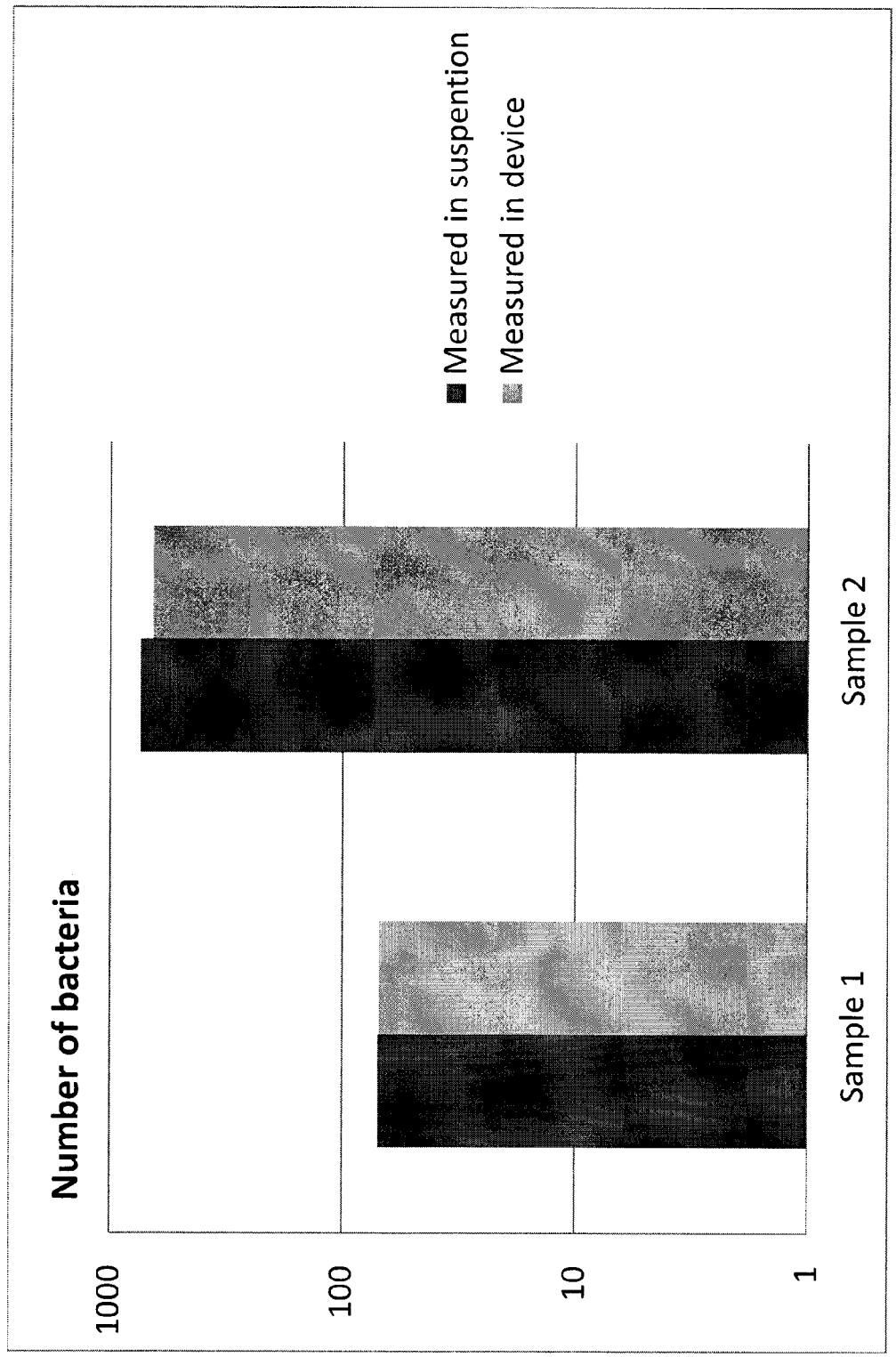

FIG. 19 discloses a chart for Example 2.

Figure 20:
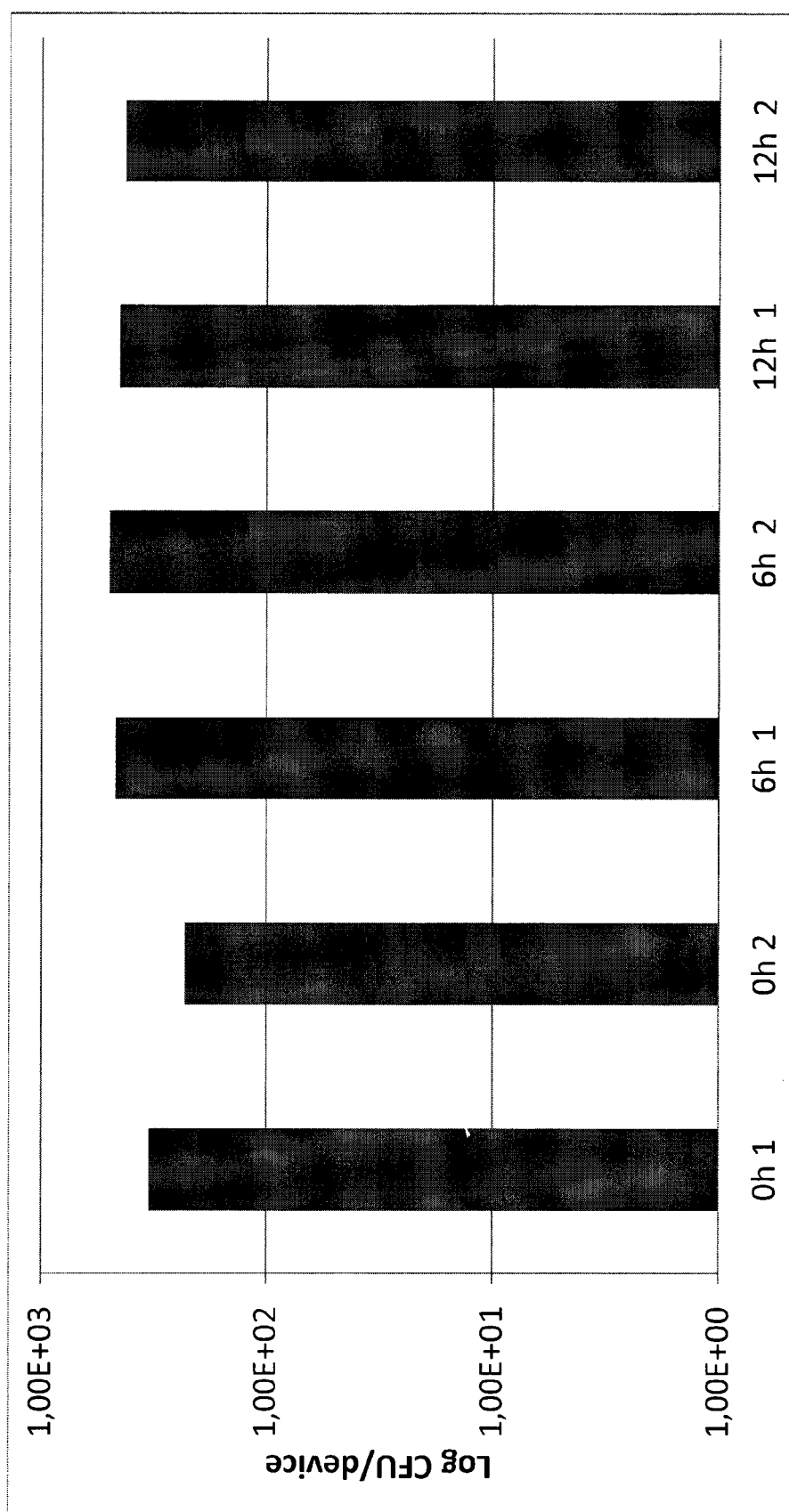

FIG. 20 discloses a chart for Example 3.

DETAILED DESCRIPTION

An embodiment of a urine sampling device is disclosed in FIGS. 1 and 2. The figures disclose a transparent sheet comprising two layers. A urine sampling layer 3 and a support layer 4. The support layer 4 has optionally a grid pattern 2 as seen in FIG. 3.

The fluid sampling layer 3 has liquid receiving and retaining properties by means of capillary forces and/or diffusion. This means that the layer 3 in itself can receive fluid and also hold it. This may be an important aspect for an embodiment of the disclosure, as an embodiment of the device is intended primarily for analysis of human urine, in search of any urinary tract infection (UTI). To be able to make an analysis the retention of the urine must be reproducible in particular with regard to volume that is received. And even more specific with regard to the number of bacteria that is sampled, and retained. The fluid sampling layer 3 is preferably chosen from a group consisting of polysaccharides or synthetic polymers, which are preferably hydrophilic. Optionally the polymers could be cross-linked. Examples of polysaccharides are: cellulose and starches and derivates thereof or agar. Examples of synthetic hydrophilic polymers are: polyethylenoxides, polyvinylpyrrolidones, polyvinylalcoholes or acrylate polymers.

The urine sampling layer 3 comprises preferably a hydrogel. The hydrogel can be in the form of a film or a foam. The film is to be understood to be a dry film. However should the film contain a small amount of moisture this will not affect the function of the film. The film is easily applied by spreading the gel on the support layer 4. A foam can be produced by many well-known techniques and gives a different structure.

The support layer 4 is supporting the fluid sampling layer 3. The support layer 4 optionally comprises a grid pattern 2. The grid pattern 2 is used after fluid sampling. The grid pattern 2 is used to directly count colonies of bacteria when the urine sampling device is cultivated on a cultivation device 11 as exemplified in FIG. 13. The support layer 4 is transparent. The support layer 4 can be made of several suitable materials. The support layer 4 can for example be made of a plastic material transparent in visible light (400-700 nm). If a grid pattern is provided it is added by any suitable technique known to the skilled person, for example printing, painting or applying a textile grid to the support layer 4.

By having the fluid sampling layer 3 attached to the support layer 4 comprising the grid pattern 2, the device 1 is arranged such that it can directly after having received the urine be applied to a cultivation device 11. The transparency of the formed sheet may be of importance for the usage of an embodiment of the device 1. This is due to the fact that the device is intended to be applied directly to a cultivation device, and the bacteria colonies formed after cultivation can thus be counted directly through the device 1, with aid from the grid pattern 2. This means that after sampling the device 1 is ready to be applied to a cultivation device 11 by positioning it with the fluid sampling layer 3 directly on the cultivation device 11. It should however be understood that the device 1 can also be applied on the bottom of a Petri dish and then agar can be cast over the device for cultivation.

The discussed cultivation device 11 is preferably a Petri dish provided with agar comprising bacteria nutrients for total count of aerobic or anaerobic bacteria or selective substrates for enumerating special groups of bacteria or specific bacteria species.

In FIG. 1 no grid pattern is provided to the device 1, in this case one could preferably use the device with a cultivation device 11 that has a grid pattern 2' as seen in FIG. 14. However if a grid pattern is applied to the device 1, generally no grid pattern is necessary on the cultivation device 11. But it is thinkable to apply a grid pattern to both the device 1 and to the cultivation device 11, for example for creating a finer grid pattern, or simply applying one set of lines to the urine sampling device 1 and another set of lines to the cultivation device 11, thus achieving a grid pattern at the instant when the urine sampling device 1 and the cultivation device 11 meet for cultivation.

In a further embodiment the device 1 is provided with a flap 8 as can be seen in FIG. 4 and FIG. 5. The flap 8 aids the operator of the device in keeping the device 1 uncontaminated when applying it to a hygiene absorbent product 10, see FIG. 7. The flap 8 aids also an operator in keeping the device 1 uncontaminated when applying it to a cultivation device 11. The flap 8 is preferably attached to the device 1 by means of an adhesive. The flap 8 is preferably transparent so as not to interfere with the analysis.

According to a non disclosed further development of the device 1 the support layer 4 is provided with transparent attachment means. This is preferably performed with a transparent adhesive. But the attachment means can also be any suitable device such as a mechanical attachment means in the form of for example a hook and loop arrangement. A non transparent attachment means would also be thinkable if it could be easily removable when performing the analysis. The attachment means is preferably arranged such that it attaches detachably to a top sheet of a hygiene absorbent product 10. The detachability can be obtained by means of choosing the tackability of the adhesive or for example by means of the mentioned hook and loop arrangement. The strength of the attachment of the support layer can also be tailored by adjusting the amount of attachment means, i.e. either over the whole surface or by using a discontinuous application or similar means.

In another embodiment which comprises the device 1 described above, a carrier layer 6 is positioned on the urine sampling layer 3, as can be seen in FIG. 8. The carrier layer 6 is preferably formed by a nonwoven fabric. The layer is preferably attached detachably such that it can be removed when the device 1 is to be applied on the cultivation device 11 for performing the analysis. The carrier layer 6 improves the comfort for a user. The carrier layer 6 may also improve the wicking properties of the device 1, such that the urine is more evenly distributed over the surface of the device 1, thus providing for a better analysis as the bacteria in the sample is distributed better. This means that colonies that are grown subsequently will be easier to count. The carrier layer 6 is attached to the urine sampling layer 3. This is preferably done with attachment means provided on the carrier layer, such as an adhesive or by welding e.g. ultrasonic welding. The carrier layer 6 could also be attached by adhesive forces between the carrier layer 6 and the urine sampling layer 3, for example between a carrier layer 6 made of non woven and a urine sampling layer 3 made of hydrogel.

Preferably the urine sampling device 1 has the same size and shape as a cultivation device 11. This will prevent contamination risks when applying the urine sampling device 1 to the cultivation device 11. The cultivation device 11 could be a standard Petri dish. But in order to adapt the device 1 for different body sizes and also for having a suitable spread of the urine to be sampled over the major part of the device 1, it is better to apply cultivation devices 11 having an adapted shape and form, i.e. essentially the same shape and size as the urine sampling device 1. For sampling from small sizes persons as children a smaller device 1 is preferred and consequently a non standard cultivation device 11 should be applied. As stated above the cultivation device 11 can optionally be provided with a grid pattern 2'.

In further development several devices 1 of the type described above, are attached to a carrier layer 6 as described, thus providing a urine sampling arrangement 5, as in FIGS. 9, 10, 11 and 12. FIG. 9 and FIG. 10 disclose the arrangement 5 upside down, i.e. with the side that is arranged to be attached to a hygiene absorbent product. The size of the carrier layer 6 is such that several devices 1 can be accommodated on the layer 6. This makes it possible to perform a double, triple or multiple sampling, and subsequent cultivation of the devices 1. This will mean that sampling can be performed efficiently as the application of the devices 1 can be performed in one operation. Removal can either be performed group wise or by removing the carrier layer 6 and then individually removing the devices 1 from the hygiene absorbent product. In particular FIGS. 10 and 12 disclose devices 1 with flaps 8 attached to the devices for individual removal of the devices 1. It is also possible to use the arrangement for performing different tests on the sampled urine. For example one device 1 of the arrangement 5 for determining the total number of aerobe bacteria, another for determining the number of *E. coli* and a further device 1 for yet another analysis. Even though the figures discloses a number of three devices in the arrangement, the disclosure should not be construed as limited to this number, two, four or any suitable number is possible.

In a preferred body sampling system the device 1 or arrangement 5 is supplied with a container 12 for housing the device 1 or arrangement 5, after sampling. The container should be sterile, and preferably the device 1 or arrangement 5 and the container are packed together in a sterile way with a cultivation device 11. That is the urine sampling device 1 and the cultivation device 11 should preferably be packed in two separate sterile packs so that when using the device 1 and opening the pack this will not contaminate the cultivation device 11. This thus provides a complete kit for analysing urine as seen in FIGS. 15 and 16. Preferably the cultivation device 11 has the same size a shape as the device 1 or arrangement, such that cultivation can be performed without contamination risks. These risks would occur if the cultivation device 11 is larger than the sampling device 1 or arrangement 5, and the operator could contaminate areas of the device 1 projecting outside the device 1 when applying the device to the cultivation device 11.

It is also possible to provide a kit where no cultivation device 11 is provided. Such a kit would be preferred when analysis is not performed close to the sampling, in which case the cultivation device 11 need not be sent with the device 1 to the testing laboratory.

A hygiene absorbent product 10 as seen in FIG. 5, 6 or 10 and 11 could be distributed with the device 1 or arrangement 5, preinstalled. This has the advantages that risk of contamination when applying the device to a hygiene absorbent product can be eliminated.

An embodiment of the disclosure also involves a method for sampling of urine for analysis comprising the steps of:
 a applying a device 1 according to the above, to a hygiene absorbent product;
 b applying the hygiene absorbent product as modified to a user;
 c await delivery of urine from the user;
 d removing the hygiene absorbent product from the user; and
 e removing the device 1 from the hygiene absorbent product;
or
 a1 applying an urine sampling arrangement 5 according to the above, to a hygiene absorbent product;
 b1 applying the hygiene absorbent product as modified to a user;
 c1 await delivery of urine from the user;
 d1 removing the hygiene absorbent product from the user; and
 e1 removing the arrangement 5 from the hygiene absorbent product;
or
 a2 providing a hygiene absorbent product with a urine sampling device 1 preinstalled;
 b2 applying the hygiene absorbent product to a user;
 c2 await delivery of urine from the user;
 d2 removing the hygiene absorbent product from the user; and
 e2 removing the device 1 or arrangement 5 from the hygiene absorbent product.

An embodiment of the disclosure further comprises the steps of:
 f applying the device 1 to a cultivation device 11 with the urine sampling layer 3 positioned on the cultivation device 11;
 g cultivating the sample under predetermined controlled conditions; and
 h determining the amount of bacteria in the sample by controlling the number of colonies counted through the transparent device 1;
or
 f1 applying the arrangement 5 to a cultivation device 11 with the urine sampling layer 3 positioned on the cultivation device 11;
 g1 cultivating the sample under predetermined controlled conditions; and
 h1 determining the amount of bacteria in the sample by controlling the number of colonies counted through the transparent device 1.

The disclosure is further understood by the following non limiting examples:

Example 1

Testing a Sampling Device According to an Embodiment of the Disclosure

The main principle for an embodiment of the urine sampling device is that a specific amount is absorbed and kept in the device from first urination. This is important for a correct measurement. For best result the device should be independent of amount of urine in first urination and independent of number of urinations before the device is taken off and analysed—it should measure the correct and same numbers of bacteria.

In this test a carboxymethylcellulose gel was applied on to a plastic film and exposed to different amounts of test liquid and different numbers of "urinations". The specimen was weighted before and after "urination" and the net weight as well as the counted number of colonies on each device are shown in the table below.

The carboxymethylcellulose gel was produced as follows:

A 2% (w/w) water solution of carboxymethylcellulose (CMC) from Hercules (Blanose Cellulose Gum) was prepared by dispersing the powder in water and subsequently stirring the solution for at least 12 hrs. The solution was then transferred to a transparent plastic film using a doctor blade technique. The film was left to dry in room temperature overnight. Samples with a diameter of 4.5 cm was punched from the film and applied in the example.

The test liquid used was TSB (Tryptone Soy Broth) in saline (1:9) with the addition of an E. coli (about $10^3$ CFU (Colony Forming Units)/ml, CCUG 49263, NCTC 10538). The pouring was done gently with a beaker from 1 cm above the surface.

| Specimen nr: | Performed pouring | Net weight gain (g) | CFU/device |
|---|---|---|---|
| 1 | 10 ml (once) | 0.3956 | 245 |
| 2 | 30 ml (once) | 0.5849 | 188 |
| 3 | 100 ml (once) | 0.7925 | 265 |
| 4 | 10 ml + 10 ml (two times) | 0.7276 | 304 |
| 5 | 100 + 100 ml + 100 ml (large volume three times) | 0.8033 | 110 |

Log. CFU/device is also visualized in FIG. 18.

The conclusion is that the device is relatively robust. Net weight differs a bit in these trials but log CFU/device is relatively constant independent of amount "urine" and number of "urinations".

Example 2

Testing Different Concentrations of Bacteria in the "Urine"

It is also of importance that the amount of bacteria measured is correct. In this test the concentration of E. coli (CCUG 49263, NCTC 10538) in TSB in saline (1:9) was measured with traditional pour plate directly from the solution and compared to the measured amounts on a fluid sampling device of an embodiment of the disclosure. In this case the specimen was made from a CMC gel dried on to a plastic film.

Four test specimens were "urinated" with 10 ml of E. coli with four different concentrations according to the table below. 999 depict that the number of colonies were too many to be counted. Dilutions of an overnight culture of E. coli, were made in tenfold steps to achieve the different concentrations of Sample 1-4

| Sample number | Measured in solution (CFU/ml) | Net weight of device after "urination" (g) | Measured on Easy Count device. (CFU/ml) |
|---|---|---|---|
| Sample 1 | 70 | 0.5047 | 69 |
| Sample 2 | 740 | 0.5871 | 656 |
| Sample 3 | 999 | 0.4687 | 999 |
| Sample 4 | 999 | 0.6287 | 999 |

In practice 10 ml of E. coli solution was poured on to the specimen mounted on the surface of an incontinence product. A certain amount was absorbed by the gel (net weight in table). 2 minutes after urination the specimen was dismounted and put upside down on the surface of TSA. After incubation in 37° C. two days colonies were counted directly through the transparent plastic support. Results from the two concentrations that were countable can be seen in FIG. 19.

Two concentrations were not measurable in this test, as seen in table above, the reason for this was that too low dilutions where put on the agar dish in the suspension test and too many colonies grew on the urine sampling device—for easy counting. This can be solved by thinner gels—absorbing less amount of liquid—and hence resulting in lower number of colonies. But it depends on the target for the test—The device has to be designed to measure the critical concentration. In particular the device must be designed with regard to the number of total aerobic bacteria to be detected, for example the total number of E. coli to be detected as a diagnosis of UTI (Urinary Tract Infection). The device used in this test was adapted to such if $10^3$ CFU/ml is a critical value.

For the two concentrations as measured above, the results are very similar comparing numbers measured directly from suspension and numbers measured using the urine sampling device.

Example 3

Three Different Cases of Urination

The purpose of this experiment was to evaluate the stability of the fluid sampling device. It was to investigate if the device could handle that a person urinates more than once, and the influence of this on the final result.

In this test a CMC gel was produced as described in Example 1. It was challenged with both different amounts of "urine" and different times between urination and start of analyze. The test was performed with duplicates. The "urine" was TSB diluted (1:9) in saline. The test organism was E. coli (CCUG 49263, NCTC 10538). The test bacteria was grown over night in TSB and diluted till approx. $10^3$ CFU/ml in the test "urine".

With the dried agar side up and the plastic side down the specimen was placed on a soft wadding material in an open plastic disc. 10 ml of the test urine with E. coli was poured with a pipette directly to the agar side.

The first two specimens were just after "urination" left to swell for 1-2 minutes and then placed upside down (gel side down) on to an agar gel with nutrition (TSA). This procedure was done to simulate a person urinating on the product and where the product subsequently is taken off and wherein the analysis is begun closely in time after this. This procedure is annotated 0 hours in FIG. 20.

The next two specimens were exposed to 10 ml "urination" in the same way, left to stay in 37° C. and after 6 hours exposed to a second "urination. The samples were left to stay for 6 more hours in 37° C. and finally put in contact with TSA after 12 hours. This procedure was done to simulate a person urinating directly on the product and a second time after 6 hours and finally the product taken off in the morning after 12 hours. This is annotated 6 hours in FIG. 20.

The last two specimens were exposed to 10 ml "urination" in the same way and let to rest for 12 hours in 37° C. before put in contact with TSA and starting the cultivation. This procedure was done to simulate a person urinating directly on the product and the product was taken off in the morning after 12 hours. This is annotated called 12 hours in FIG. 20.

After incubation in 37° C. in two days the number of colonies was counted through the plastic support and the result can be seen in FIG. 20.

The conclusion is that there are very small differences between the different cases and this will not influence the diagnosis of for ex. UTI.

The invention claimed is:

1. A urine sampling system comprising:
   a cultivation device; and
   a urine sampling device that comprises:
   a transparent sheet comprising two layers, namely,
   a urine sampling layer and
   a support layer,
   wherein the urine sampling layer has liquid receiving and retaining properties by means of capillary forces and/or diffusion, and the support layer is provided with an attachment means, wherein the attachment means is configured to attach detachably to a top sheet of a hygiene absorbent product; and
   wherein the urine sampling device is configured to be selectively positioned on the to sheet of the hygiene absorbent product and then positioned on the cultivation device for cultivation of any bacteria in the urine sampling layer.

2. The urine sampling system according to claim 1, which sheet, by being transparent, allows counting of bacteria on the sampling device while the sampling device is applied directly to the cultivation device.

3. The urine sampling system according to claim 1, wherein the urine sampling layer has no auxiliary addition of bacteria nutrients.

4. The urine sampling system according to claim 1, wherein the urine sampling layer comprises a hydrogel in the form of a film or a foam.

5. The urine sampling system according to claim 1, wherein the urine sampling layer comprises a liquid retaining material, chosen from a group consisting of polysaccharides or synthetic polymers.

6. The urine sampling system according to claim 1, wherein the device comprises a flap configured for removal of the device from a hygiene absorbent product and for positioning the device on a cultivating device, after a urine sample has been collected.

7. The urine sampling system according to claim 1, wherein the support layer is provided with a transparent attachment means.

8. The urine sampling system according to claim 7, wherein the attachment means is provided in the form of a transparent adhesive.

9. The urine sampling system according to claim 7, wherein the attachment means is arranged such that the device is detachable.

10. The urine sampling system according to claim 1, wherein the device is provided with a carrier layer positioned on the urine sampling layer.

11. The urine sampling system according to claim 10, wherein the carrier layer is provided with an attachment means for detachably attaching the carrier layer to the urine sampling layer.

12. The urine sampling system according to claim 1, wherein the urine sampling device has a size that is configured for use with the cultivation device, such that the urine sampling device can be applied directly to the cultivation device.

13. The urine sampling system according to claim 1, wherein the support layer comprises a grid pattern.

14. Urine sampling arrangement, wherein a group of urine sampling devices according to claim 1 have been attached to a carrier layer such that the group of devices can be employed together.

15. Urine sampling system, comprising a device according to claim 1, and further comprising a container for housing the urine sampling device, when transporting the urine sampling device to a cultivation site.

16. The system according to claim 1, wherein the cultivation device comprises a grid pattern.

17. Hygiene absorbent product comprising a urine sampling device according to claim 1.

18. Method of sampling urines for analysis comprising the steps of:
   a applying a urine sampling device according to claim 1 to a hygiene absorbent product;
   b applying the hygiene absorbent product as modified to a user;
   c await delivery of urine from the user;
   d removing the hygiene absorbent product from the user; and
   e removing the urine sampling device from the hygiene absorbent product.

19. Method according to claim 18, wherein the method further comprise the steps of:
   f applying the urine sampling device to the cultivation device with the urine sampling layer positioned on the cultivation device;
   g cultivating the sample under predetermined controlled conditions; and
   h determining the amount of bacteria in the sample by controlling the number of colonies counted through the transparent device.

* * * * *